United States Patent [19]

Ogasawara

[11] Patent Number: 4,674,497
[45] Date of Patent: Jun. 23, 1987

[54] MEDICAL LASER DEVICE
[75] Inventor: Tadahiko Ogasawara, Tokyo, Japan
[73] Assignee: Olympus Optical Co., Ltd., Tokyo, Japan
[21] Appl. No.: 757,748
[22] Filed: Jul. 22, 1985
[30] Foreign Application Priority Data
Aug. 15, 1984 [JP] Japan ................... 59-170169
[51] Int. Cl.[4] .................................. A61B 17/35
[52] U.S. Cl. ................................... 128/303.1
[58] Field of Search ............ 128/4, 6, 303.1, 395–398, 128/205.12, 205.27, 205.29

[56] References Cited
U.S. PATENT DOCUMENTS

| 2,702,089 | 2/1955 | Engelder ................. 128/205.27 |
| 3,659,613 | 5/1972 | Bredemeier ................. 128/395 |
| 3,906,953 | 9/1975 | Wallace et al. ................. 128/303.1 |
| 4,032,311 | 6/1977 | Bohmrich et al. ................. 128/205.29 |
| 4,086,923 | 5/1978 | Henkin ................. 128/205.12 |
| 4,090,513 | 5/1978 | Togawa ................. 128/205.12 |
| 4,146,019 | 3/1979 | Bass et al. ................. 128/6 |
| 4,181,512 | 1/1980 | Kippel et al. ................. 128/205.29 |
| 4,211,229 | 7/1980 | Wurster ................. 128/303.1 |
| 4,313,431 | 2/1982 | Frank ................. 128/303.1 |
| 4,329,980 | 5/1982 | Terada ................. 128/4 |
| 4,418,688 | 12/1983 | Loeb ................. 128/6 |
| 4,470,407 | 9/1984 | Hussein ................. 128/303.1 |
| 4,499,895 | 2/1985 | Takayama ................. 128/6 |
| 4,519,390 | 5/1985 | Horne ................. 128/395 |
| 4,550,240 | 10/1985 | Toida et al. ................. 128/303.1 |

FOREIGN PATENT DOCUMENTS 2837281 3/1980 Fed. Rep. of Germany ............ 128/205.27

OTHER PUBLICATIONS

IEEE Transactions on Biomedical Engineering, vol. BME-25, No. 3, May 1978, Seiten 219-224-"Use of Gas Jet Appositional Pressurization in Endoscopic Laser Photocoagulation".

Primary Examiner—Kyle L. Howell
Assistant Examiner—Max F. Hindenburg
Attorney, Agent, or Firm—Frishauf, Holtz, Goodman & Woodward

[57] ABSTRACT

A medical laser device includes a device body and a laser probe connected to the body. In the device body are arranged a laser source for emitting laser beams and an air pump. The laser probe has an outer tube, a laser guide extending through the tube, and an air supply passage defined between the inner surface of the tube and laser guide. The laser beams emitted from the laser source are guided through the laser guide and ejected from the distal end of the laser guide. A drying unit is connected to the discharge side of the pump. Air streams are supplied from the pump to the air supply passage after being dried by the drying unit, and then ejected from the air supply passage toward the distal end of the laser guide.

6 Claims, 8 Drawing Figures

4,674,497

MEDICAL LASER DEVICE

BACKGROUND OF THE INVENTION

This invention relates to a medical laser device, and more particularly to a medical laser device provided with air-feeding means. When laser treatment is applied to an internal organ, for example, the stomach in the coeliac cavity by means of a medical laser device, a laser probe is inserted into the coeliac cavity. Laser beams are irradiated through said laser probe. When, however, laser beams are sent into the coeliac cavity, smoke emanating from the burned organization, and blood and viscous liquids scatter from the walls of the coeliac cavity, and settle on the laser emitting end of the laser probe. When the scattered mass is attached to the laser emitting end, the laser energy is absorbed in the deposited scattered mass, thereby generating a large amount of heat at the emitting end and leading to damage of the laser probe.

To avoid the above-mentioned drawbacks, there has been proposed a laser device which is designed to eject air streams from the tip of the laser probe to prevent the particles scattered with the coeliac cavity wall from being deposited on the tip of the laser emitting end. In this device, the air streams are produced by sucking air by an air pump and compressing it thereby, and supplying it to the air supply passage of the laser probe by the pump.

Since, however, the air is supplied after being compressed by the air pump, air moisture is condensed into water particles. The water particles are carried through the air supply passage to the tip of the laser probe. When water particles settle on the laser emitting end, the laser beams undergo irregular reflections or refractions. Thus, the laser beams are prevented from being converged on the desired spot in the coeliac cavity, and irradiated on the tip of the laser probe to damage it.

SUMMARY OF THE INVENTION

This invention has been accomplished in view of the above-mentioned drawbacks, and is intended to provide a medical laser device which prevents water particles from being generated at the laser probe tip, thereby suppressing the irregular reflections and refractions of laser beams.

To attain the above-mentioned object, the present invention provides a medical laser device which comprises:

a laser source for emitting laser beams;

air supply means for supplying air streams;

a laser probe provided with a laser guide, having a laser emitting end, for guiding the laser beams emitted from the laser source and emitting the laser beams from the emitting end, and an air supply passage allowing for the passage of air streams drawn off from the air pump and the ejection of said air streams to the vicinity of the emitting end of the laser guide; and drying means, set between the air pump and laser probe, for drying the air streams conducted from the air pump.

BRIEF DESCRIPTION OF THE DRAWINGS

FIGS. 1 to 5 illustrate a laser device according to an embodiment of the present invention, in which FIG. 1 is a perspective view of the device, FIG. 2 is a sectional view schematically showing the entire device, FIG. 3 is a cross sectional view of a drying unit, FIG. 4 is an exploded side view of a laser probe, and FIG. 5 is an enlarged sectional view of the laser probe tip;

DETAILED DESCRIPTION OF THE PREFERRED EMBODIMENTS

Figure 1:
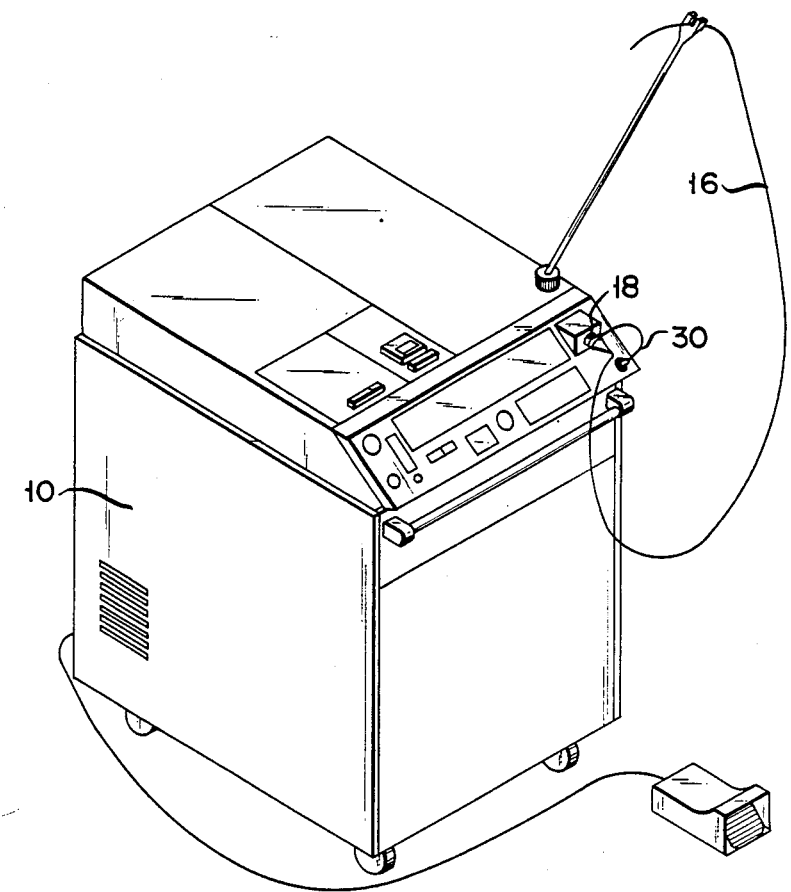
Figure 2:
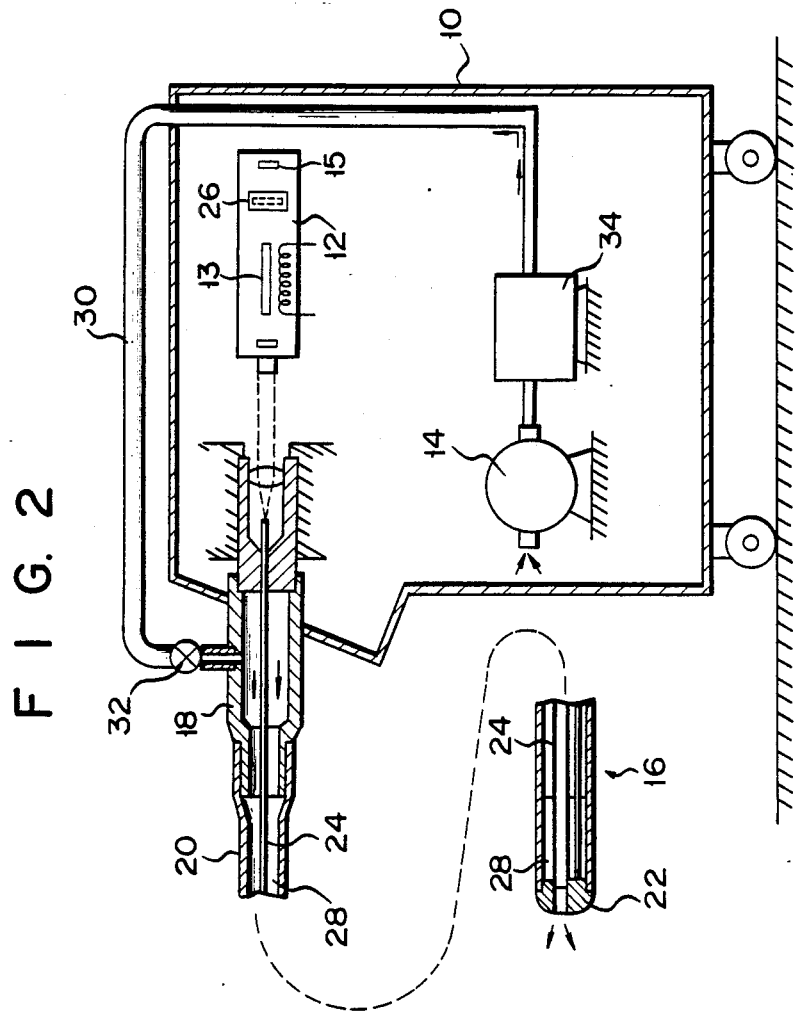

Description may now be made with reference to the accompanying drawings of a medical laser device embodying this invention. As seen from FIGS. 1 and 2, the subject medical laser device comprises a device body 10, wherein a laser source 12 and an air pump 14 are disposed. The device body 10 is connected to a laser probe 16 for conducting laser beams into the coeliac cavity of a patient. The laser probe 16 includes an outer tube 20 connected at one end to the device body 10 by means of a connector 18. The distal end of the outer tube 20 is fitted with a nozzle 22. A laser guide 24 extends through the outer tube 20 from the connector 18 to the nozzle 22. Laser beams delivered from the source 12 are ejected from the nozzle 22 while being conducted through the guide 24. The laser source 12 is provided with a laser rod 13, a resonance mirror 15, and a shutter 26 between them. The emission of a laser beam from the source 12 is controlled by the shutter 26.

In the laser probe 16, an air supply passage 28 is defined between the inner surface of the outer tube 20 and laser guide 24 and extends from the connector 18 to the nozzle 22. An air pipe 30 is set between the connector 18 and the discharge side of the air pump 14. The air supply passage 28 communicates with the air pump 14 through the air pipe 30. A valve 32 for opening and closing the air pipe 30 is provided on that side of the air pipe 30 which faces the connector 18. A drying unit 34 is set on the air pipe 30 between the valve 32 and air pump 14. Accordingly, air streams flowing from the air pump 14 are supplied to the air supply passage 28 of the laser probe 16 through the air pipe 30, after being dried by the drying unit 34, and later ejected to the outside at the nozzle 22 after being conducted through the air supply passage 28.

Figure 3:
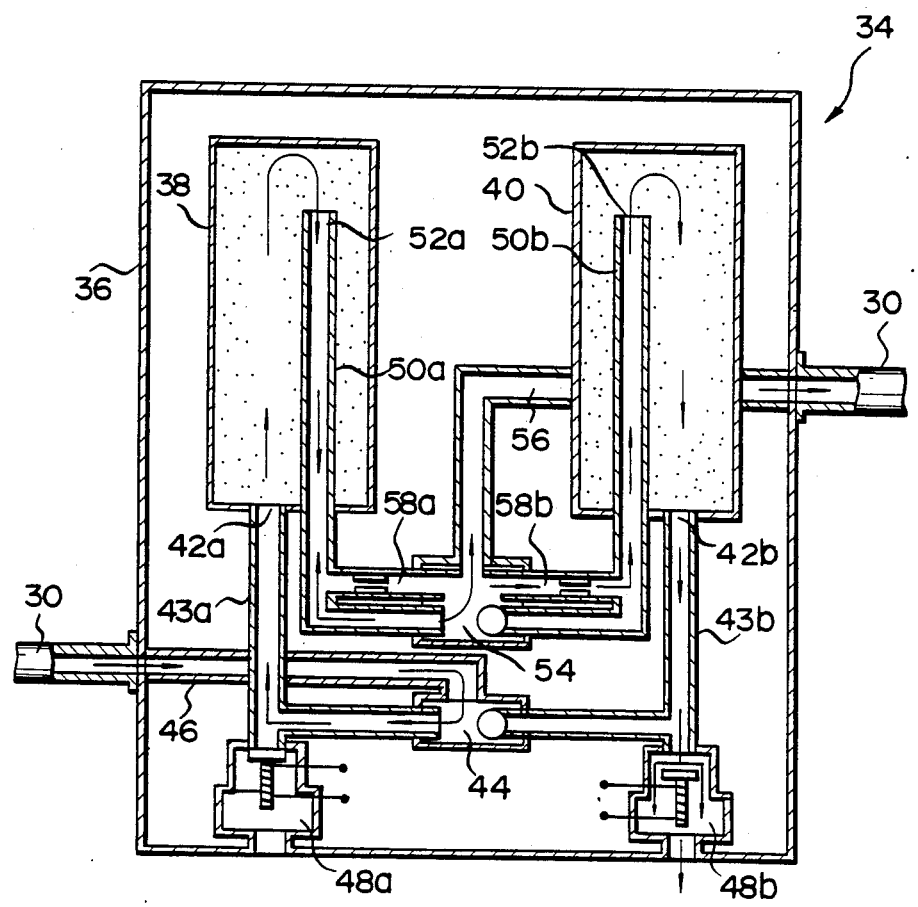

As seen from FIG. 3, the drying unit 34 consists of a drying agent type dryer. The drying unit 34 comprises an outer case 36 and first and second drying cylinders 38, 40 held in the outer case 36. These drying cylinders 38, 40 are filled with silica gel acting as a drying agent. The drying cylinders 38, 40 are respectively provided with bottom ports 42a, 42b. The bottom port 42a of drying cylinder 38 communicates with the air pipe 30 through a connection pipe 43a, influx side changeover valve 44 and influx pipe 46. The bottom port 42b of drying cylinder 40 communicates with the air pipe 30 through a connection pipe 43b, the changeover valve 44 and influx pipe 46. The connection pipes 43a, 43b communicate with the outside of the outer case 36 respectively through the exhaust valves 48a, 48b. A connection pipe 50a is inserted into the drying cylinder 38, and the top end of the connection pipe 50a constitutes an upper port 52a of the drying cylinder 38. The connection pipe 50a communicates with the air pipe 30 through an exhaust side changeover valve 54 and exhaust pipe 56. A connection pipe 50b is inserted into the drying cylinder 40, and the top end of the connection pipe 50b constitutes an upper port 52b of the drying cylinder 40. The connection pipe 50b communicates with the air pipe 30 through the changeover valve 54 and exhaust pipe 56. An orificed bypass pipe 58a is provided between the exhaust changeover valve 54 and connection pipe 50a. An orificed bypass pipe 58b is provided between the exhaust changeover valve 54 and connection pipe 50b.

When the influx changeover valve 44 and exhaust changeover valve 54 are set in the positions indicated in FIG. 3, air streams delivered from the air pump 14 are carried into the first drying cylinder 38 through the influx pipe 46, changeover valve 44 and connection pipe 43a. The air streams whose moisture is absorbed by the drying agent are carried into the air pipe 30 through the connection pipe 50a, exhaust valve 54 and exhaust pipe 56. Part of the dried air streams are brought into the second drying cylinder 40 through the bypass pipe 58b and connection pipe 50b. After removing moisture from the drying agent in the second drying cylinder 40, the part of the dried air streams is discharged to the outside through the connection pipe 43b and exhaust valve 48b.

As mentioned above, the drying unit 34 is so designed that while air streams are dried by one of the two drying cylinders, the drying agent held in the other drying cylinder is regenerated by being dried by part of the previously dried air streams. Consequently, the drying unit 34 can continuously dry the air streams delivered from the air pump 14 for many hours, by periodically changing the operation of the influx changeover valve 44 and exhaust changeover valve 54.

Figure 4:
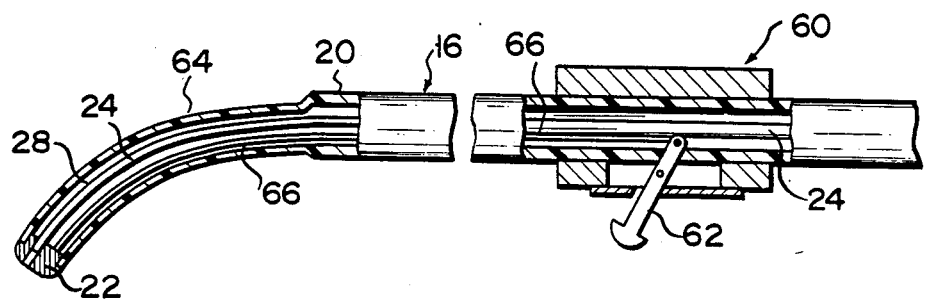
Figure 5:
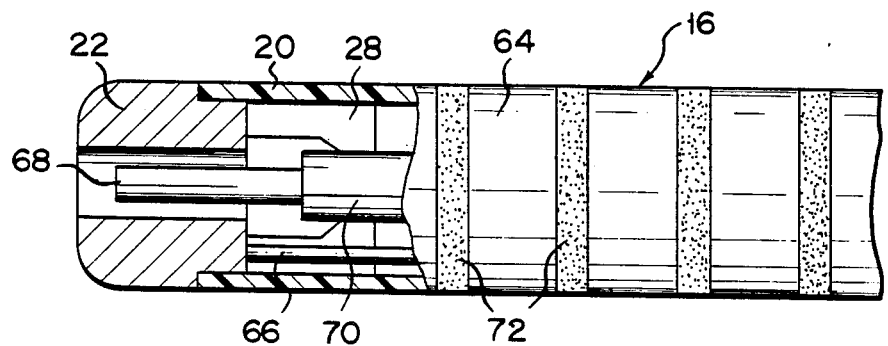

Referring to FIGS. 4 and 5, the laser probe 16 includes an operation section 60 set in the intermediate part of the outer tube 20. An operation lever 62 is rockably fitted to the operation section 60. The distal end portion of the outer tube 20 is made thin to constitute a flexible portion 64. An operation wire 66 extends through the outer tube 20, and is connected at one end to the operation lever 62 and at the other end to the nozzle 22. When, therefore, the operation lever 62 is rocked either to pull or push the operation wire 66, the flexible portion 64 of the laser probe can be turned in any desired direction.

As seen from FIG. 5, the laser guide 24 includes a core 68 composed of an optical fiber and an outer covering 70 surrounding the outer peripheral surface of the core 68. A scale 72 is formed on the outer peripheral wall of that portion of the outer tube 20 which falls within the range between the nozzle 22 and the boundary set apart therefrom at a prescribed distance. The scale units are all formed of concave or convex portions or indicated in a color distinguishable from the surroundings. It is preferred that the scaled region be formed over a range measuring more than 50 mm from the distal end of the laser probe and the respective scale units be pitched at a distance ranging from 1 to 10 mm. When the scale 72 is applied to measure the depth of a hole to be formed in the coeliac cavity for the medical treatment by the laser probe 16, it is preferred that the scaled region be formed over a longer range than 50 mm with the respective scale units pitched at a distance from 1 to 5 mm.

Description may now be made of the operation of the laser device constructed as described above. When medical treatment is performed by means of the laser device, an endoscope is first inserted into the coeliac cavity. Then the laser probe 16 is introduced through the forceps channel of the endoscope. The distal end of the laser probe 16, that is, its nozzle 22 is allowed to protrude from the distal end of the endoscope. Since the distal end portion of the laser probe 16 is provided with the scaled region 72, it can be ascertained whether the distal end of the laser probe projects from the tip of the endoscope. After the laser probe nozzle 22 is turned in a prescribed direction by means of the operation lever 62, the laser source 12 and air pump 14 are actuated. When the shutter 26 is opened a laser beam delivered from the laser source 12 is carried into the affected portion of the coeliac cavity through the central port of the nozzle 22, while being guided by the laser guide 24. At this time, the air pump 14 sucks air from the outside of the laser device body 10. The air is supplied to the air pipe 30 while being compressed. The compressed air is supplied to the drying unit 34 to be dried. The dried air is brought to the changeover valve 32 through the air pipe 30. When the valve 32 is opened, the dried air streams flow into the air supply passage 28 through the connector 18, then to the distal end of the laser probe 16 and last are ejected to the outside through the central hole of the laser probe nozzle 22.

The laser device constructed as described above offers the advantages that it sends forth not only laser beams but also air streams through the nozzle 22 at the time of medical treatment, thereby preventing, for example, blood or viscous coeliac fluids from being deposited on the distal end of the laser guide. Moreover, the air ejected from the laser probe nozzle 22 is dried by the drying unit 34 in advance, thus preventing water droplets from being formed on the inner wall of the nozzle 22 or at the distal end portion of the laser guide 24. Consequently, laser beams emitted from the distal end of the laser guide 24 are prevented from being subjected to irregular reflections or refractions, and the laser beams can be assuredly ejected in any desired direction. As a result, the laser probe 16 is prevented from being damaged. Further, the distal end portion of the laser probe 16 can be flexed in any desired direction by the actuation of the operation lever 62, thereby enabling laser beams to be perpendicularly ejected to the inner wall of the bronchial tube or alimentary canal.

Figure 6:
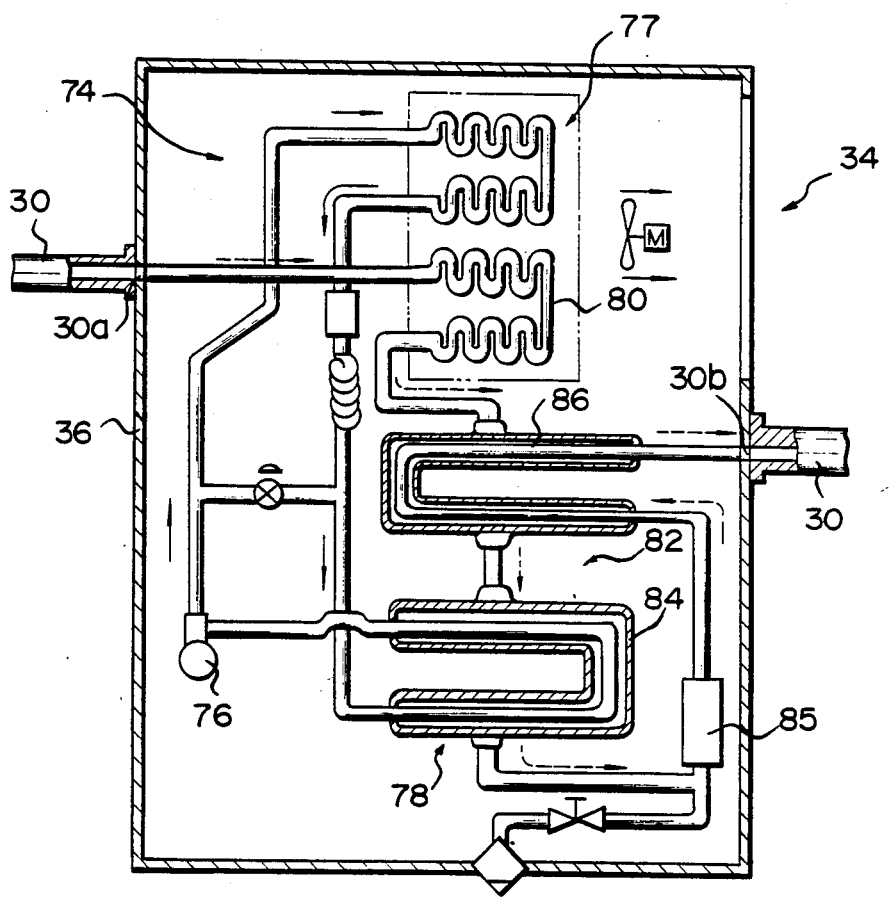
FIG. 6 is a side view of a modification of a drying unit.

The medical laser device of this invention is not limited to the above-mentioned embodiments, but is applicable with various modifications without departing from the scope and object of the invention. For instance, the drying unit 34 of the foregoing embodiments which consisted of a drying agent type drier need not be limited to such type as shown in FIG. 3, but may be remodeled as indicated in FIG. 6. The drying unit 34 of FIG. 6 comprises a refrigeration cycle 74 enclosed in an outer casing 36. This refrigeration cycle 74 includes a compressor 76, condenser 77, and evaporator 78 connected in succession. An aftercooler 80 is set near the condenser 77. This aftercooler 80 is connected at one end to the air pipe 30 through an inlet port 30a and at the other end to the outer tube 84 of a precooler 82. The outer tube 84 is set outside of the evaporator 78, and connected to the inner tube 86 of the precooler 82 through a drain separator 85. The inner tube 86 communicates with the air pipe 30 through the outlet port 30b of the outer casing 36.

The drying unit 34 of FIG. 6 constructed as described above is characterized in that wet air streams delivered from the air pump 14 pass through the aftercooler 80 and the outer tube 84 of the precooler 82 in succession to be freed of moisture by cooling, then run through the inner tube 86 of the precooler 82 to be heated, and thereafter are carried into the air pipe 30 at the outlet port 30b. Therefore, the drying unit 34 can remove moisture from air streams supplied from the air pump without reducing the temperature thereof.

Figure 7:
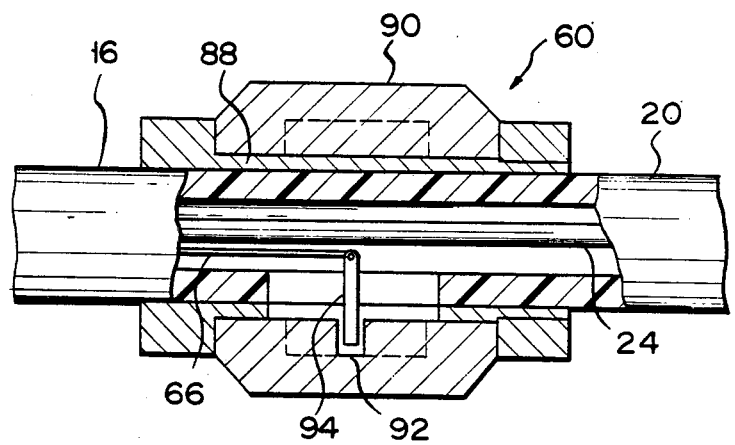
FIGS. 7 and 8 are sectional views of the various modifications of the subject laser device.

Description may now be made with reference to FIG. 7 of a modification of the operation section 60 of FIG. 4. The operation section 60 according to the modification of FIG. 7 has a fixed ring 88 engaged with the outer periphery of the outer tube 20 and a ring 90 rotatably fitted to the outside of the fixed ring 88. A helical groove 92 is formed in the inner surface of the rotatable ring 90. A pin 94 is engaged at one end with the helical groove 92, and is connected at the other end to the operation wire 66.

With the modified operation section 60, the rotation of the rotatable ring 90 causes the pin 94 to be shifted axially of the outer tube 20, thereby enabling the distal end portion of the laser probe 16 to be turned in any desired direction by means of the operation wire 66.

Figure 8:
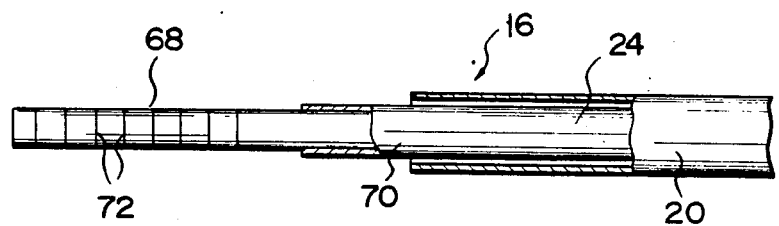

In the aforementioned embodiment, a scale 72 is provided on the outer peripheral wall of the laser probe 16. However, as shown in FIG. 8, it is possible to let the core 68 of the laser guide 24 protrude from the distal end of the outer tube 20 and impress a scale 72 on the outer peripheral surface of the distal end portion of the core 68. Further, the shape of the distal end portion of the core 68 need not be limited to a round columnar form, but may take a spherical or round conical shape.

What is claimed is:

1. A medical laser device comprising:
   a laser source for emitting laser beams;
   air supply means for conducting air streams;
   a laser probe including a laser guide, having a laser emitting end, for guiding laser beams delivered from the source and emitting the laser beams from the emitting end, and an air supply passage through which air streams supplied from the air supply means are emitted to the vicinity of the emitting end portion of the laser guide; and
   drying means, arranged between the air supply means and the laser probe, for drying air streams sent forth from the air supply means, said drying means including first and second vessels, each filled with a drying agent, guiding means for carrying air streams delivered from the air supply means into the air supply passage through the first vessel, and also for conducting part of the air streams passed through the first vessel out of the drying means through the second vessel, and valve means arranged in the guiding means, for allowing said guide means to carry air streams delivered from the air supply means into the air supply passage through the second vessel and also to conduct part of the air streams passed through the second vessel out of said drying means through the first vessel.

2. The medical laser device according to claim 1, wherein said laser probe includes an outer tube extending along the outside of the laser guide; and said air supply passage is defined by the inner surface of the outer tube and the laser guide.

3. The medical laser device according to claim 2, wherein a distal end portion of said outer tube which is positioned near the emitting end of the laser guide is made flexible; and said laser probe includes operation means for actuating the distal end portion of the outer tube by remote control to flex the distal end portion in any desired direction.

4. The medical laser device according to claim 3, wherein said operation means includes an operation lever rotatably fitted on the outer tube at a prescribed distance from the distal end portion of the outer tube; and an operation wire which extends through the outer tube to effect connection between the operation lever and the distal end portion of the outer tube.

5. The medical laser device according to claim 3, wherein said operation means includes a pin movably set on the outer tube at a prescribed distance from the distal end portion of the outer tube, an operation wire extending through the outer tube to effect connection between the distal end portion of the outer tube and the pin, and a ring rotatably fitted to the outer tube and engaged with the pin to effect its movement.

6. The medical laser device according to claim 2, wherein said laser probe includes a scale formed on the outer peripheral wall of the outer tube over a region extending from the distal end thereof to a prescribed boundary.

* * * * *